United States Patent
Kakimoto et al.

(10) Patent No.: US 8,153,823 B2
(45) Date of Patent: Apr. 10, 2012

(54) 2-ALKENYL-3-AMINOTHIOPHENE DERIVATIVE AND PROCESS FOR PRODUCING THEREOF

(75) Inventors: Takeshi Kakimoto, Chiba (JP); Toshio Kitashima, Omuta (JP)

(73) Assignee: Mitsui Chemicals, Inc., Minato-Ku, Tokyo (JP)

(*) Notice: Subject to any disclaimer, the term of this patent is extended or adjusted under 35 U.S.C. 154(b) by 674 days.

(21) Appl. No.: 12/297,221

(22) PCT Filed: Apr. 11, 2007

(86) PCT No.: PCT/JP2007/000386
§ 371 (c)(1), (2), (4) Date: Oct. 15, 2008

(87) PCT Pub. No.: WO2007/122806
PCT Pub. Date: Nov. 1, 2007

(65) Prior Publication Data
US 2009/0082579 A1    Mar. 26, 2009

(30) Foreign Application Priority Data
Apr. 17, 2006    (JP) .................................. 2006-113084

(51) Int. Cl.
C07D 333/36    (2006.01)
(52) U.S. Cl. ...................................................... 549/68
(58) Field of Classification Search ..................... 549/68
See application file for complete search history.

(56) References Cited

U.S. PATENT DOCUMENTS

| | | | |
|---|---|---|---|
| 5,747,518 A | 5/1998 | Yoshikawa et al. | |
| 5,869,427 A | 2/1999 | Yoshikawa et al. | |
| 6,239,282 B1 | 5/2001 | Katsuta et al. | |

FOREIGN PATENT DOCUMENTS

| | | |
|---|---|---|
| EP | 0 737 682 B1 | 10/1996 |
| JP | 09-235282 A | 9/1997 |
| JP | 10-182642 A | 7/1998 |
| JP | 2000-327678 A | 11/2000 |
| WO | WO 2008/056538 A1 | 5/2008 |

OTHER PUBLICATIONS

McOmie, Protective Groups in Organic Chemistry, 1973, Plenum Press, p. 46-48.*
Shendage et al, Highly Efficient Stereoconservative Amidation and Deamidation of alpha-Amino Acids, 2004, Organic Letters, vol. 6, No. 21, p. 3675-3678.*
Francis Outurquin et al., "Enamine properties of 3-aminothiophene and 3,4-diaminothiophene," Bulletin de la Société Chimique de France, 1986, pp. 267-275, No. 2.
M'Hamed Berkaoui et al., "α-Vinylation of β-Aminothiophene Derivatives, Synthesis of 6-Functionalized Thieno[3,2-b]pyridines," Tetrahedron, 1998, pp. 9055-9066, Vo. 54, No. 31.
Francis Outurquin et al., "Acid Catalyzed α-Alkylation of β-Aminothiophenes Using Aldehydes and Selenophenol. Synthesis of Bis(3-amino-2-thienyl)methane Derivatives," Tetrahedron Letters, 1993, pp. 5715-5718, vol. 34, No. 36.
M'Hamed Berkaoui et al., "Acid Catalyzed α-Alkylation of β-Aminothiophenes with Aldehydes. Synthesis of 2-Alkyl 3-thiophenamines, Bis(3-amino-2-thienyl)methane Derivatives and Dithieno[3,2-b:2',3'-e]pyridines," Journal of Heterocyclic Chemistry, 1996, pp. 9-16. vol. 33, No. 1.

* cited by examiner

Primary Examiner — Andrew D Kosar
Assistant Examiner — Karen Cheng
(74) Attorney, Agent, or Firm — Buchanan Ingersoll & Rooney PC

(57) ABSTRACT

Disclosed is a method for commercially producing 2-alkenyl-3-aminothiophene derivatives, which are useful as intermediates for agricultural chemicals, at low cost. Specifically disclosed is a method for introducing alkenyl groups into the 2-position of 3-aminothiophene derivatives by reacting 3-aminothiophene derivatives represented by the general formula (2) below or salts thereof with a ketone represented by the general formula (1) below without using a protecting group. Also specifically disclosed are 2-alkenyl-3-aminothiophene derivatives (3a) to (3d) which are useful as intermediates for agricultural chemicals,

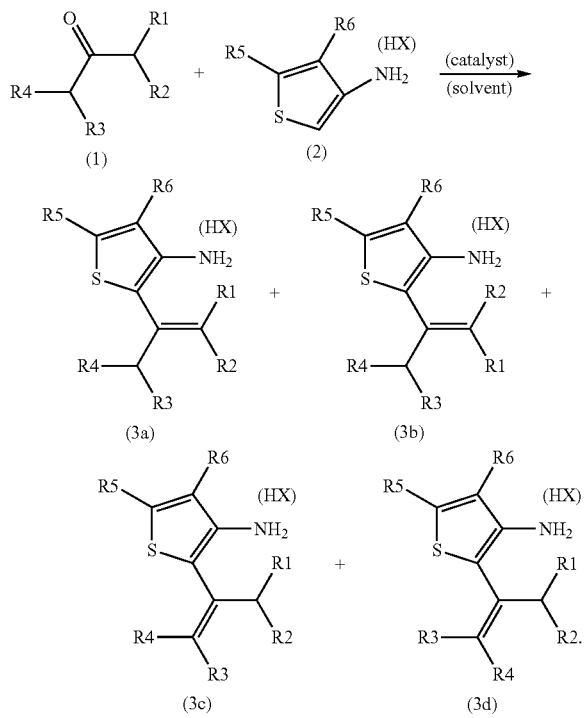

19 Claims, No Drawings

2-ALKENYL-3-AMINOTHIOPHENE DERIVATIVE AND PROCESS FOR PRODUCING THEREOF

TECHNICAL FIELD

The present invention relates to 2-alkenyl-3-aminothiophene derivatives, which are useful as fungicide for agriculture and horticulture or intermediates thereof, and a process for producing the derivatives.

BACKGROUND ART

In Japanese Patent Laid-open No. 1997-235282 (European Patent No. EP 0737682 B1), there has been described a specific kind of 2-alkyl-3-aminothiophene derivatives which has strong control effect against various plant disease and a process for production thereof. As one of processes for producing 2-alkyl-3-aminothiophene derivatives that are useful intermediates of the above compound, there has been known a process for producing it via 2-alkenyl-3-aminothiophene derivatives as intermediates by directly introducing alkyl groups into the 2-position of 3-aminothiophene derivatives. For example, in Japanese Patent Laid-open No. 2000-327678, there has been disclosed a method for synthesizing 2-alkenyl-3-aminothiophene derivatives by reacting 3-aminothiophene derivatives with various ketones and synthesizing 2-alkyl-3-aminothiophene derivatives by the reduction. However, according to the method as described in the document, to introduce alkenyl groups into the 3-aminothiophene derivatives, a formyl group, an acyl group or a carbamate group is needed as a protecting group of an amino group, and there are many rooms of improvement from the viewpoint of economical efficiency.

As a method for introducing alkyl groups into 3-aminothiophene derivatives without using a protecting group, there has been described, in Tetrahedron Letters, 34, 5715-5718 (1993), Journal of Heterocyclic Chemistry, 33, 9-16 (1996) and Tetrahedron, 54, 9055-9066 (1998), that 2-alkyl-3-aminothiophene derivatives are obtained by reacting 3-aminothiophene with various aldehydes in the presence of p-toluenesulfonic acid and selenophenol.

However, in the above documents, there has been no description of the reaction of 3-aminothiophene with a ketone.

Furthermore, in Reference Example 1 of Japanese Patent Laid-open No. 2000-327678, there has been described that when a ketone having reactivity inferior to that of aldehyde is used, 3-aminothiophene is preferentially decomposed due to its instability without progressing the reaction of the ketone with 3-aminothiophene under the conditions described therein, and desired 2-alkenyl-3-aminothiophene derivatives could not be obtained.

Patent Document 1: Japanese Patent Laid-open No. 1997-235282 (European Patent No. EP 0737682 B1)
Patent Document 2: Japanese Patent Laid-open No. 2000-327678
Non-patent Document 1: Tetrahedron Letters, 34, 5715-5718 (1993)
Non-patent Document 2: Journal of Heterocyclic Chemistry, 33, 9-16 (1996)
Non-patent Document 3: Tetrahedron, 54, 9055-9066 (1998)

DISCLOSURE OF THE INVENTION

An object of the present invention is to provide a method for commercially producing 2-alkenyl-3-aminothiophene derivatives, which are useful as intermediates for agricultural chemicals, at low cost by reacting 3-aminothiophene derivatives with ketones without using a protecting group.

In order to solve the above object, the present inventors have found 2-alkenyl-3-aminothiophene derivatives, which are useful as intermediates for agricultural chemicals, and a process for producing the derivatives, and that alkenyl groups are introduced into 2-position of 3-aminothiophene derivatives by reacting various ketones with 3-aminothiophene derivatives or salts formed from 3-aminothiophene derivatives and acids without using a protecting group. Thus, the present invention has been completed.

That is, the present invention is specified by the matters described in the following [1] to [17]:

[1] a process for producing a 2-alkenyl-3-aminothiophene derivative represented by any one of the general formulae (3a) to (3d) or a mixture thereof, in which a ketone derivative represented by the general formula (1) is reacted with a 3-aminothiophene derivative represented by the general formula (2) in the presence of an acid catalyst,

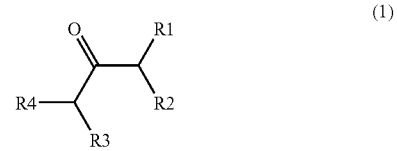

(1)

wherein, in the formula, R1, R2, R3 and R4 each independently represent a hydrogen atom, an alkyl group having 1 to 12 carbon atoms or an alkenyl group having 1 to 12 carbon atoms; at least one of R1, R2, R3 and R4 is an alkyl group having 1 to 12 carbon atoms or an alkenyl group having 1 to 12 carbon atoms; and R1 and R2, R1 and R3, R1 and R4, R2 and R3, R2 and R4, or R3 and R4 may be bonded with each other to form a cycloalkyl group,

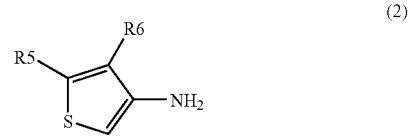

(2)

wherein, in the formula, R5 and R6 each independently represent a hydrogen atom, a halogen atom, a cyano group, a nitro group, an alkyl group having 1 to 12 carbon atoms, an alkenyl group having 1 to 12 carbon atoms, an alkynyl group having 1 to 12 carbon atoms, a phenyl group, a hetero ring, an alkoxy group having 1 to 12 carbon atoms or an alkylthio group having 1 to 12 carbon atoms; and R5 and R6 may be bonded with each other to form a cycloalkyl group,

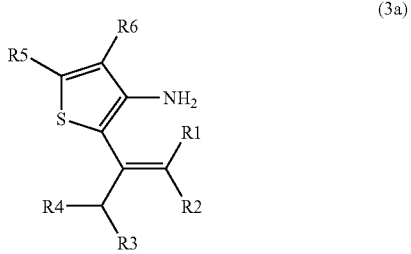

(3a)

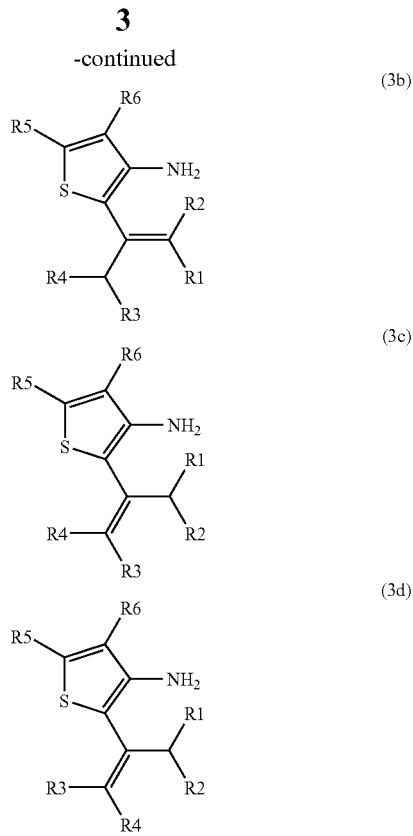

wherein, in the formula, R1, R2, R3, R4, R5 and R6 are the same as those described above;

[2] the process for producing a 2-alkenyl-3-aminothiophene derivative or a mixture thereof as set forth in [1], in which the ketone derivative represented by the general formula (1) is reacted with the 3-aminothiophene derivative represented by the general formula (2) in the absence of a solvent;

[3] the process for producing a 2-alkenyl-3-aminothiophene derivative or a mixture thereof as set forth in [1], in which the ketone derivative represented by the general formula (1) is reacted with the 3-aminothiophene derivative represented by the general formula (2) in a solvent;

[4] the process for producing a 2-alkenyl-3-aminothiophene derivative or a mixture thereof as set forth in any one of [1] to [3], in which, in the general formulae (2) and (3a) to (3d), R5 and R6 are each a hydrogen atom;

[5] the process for producing a 2-alkenyl-3-aminothiophene derivative or a mixture thereof as set forth in any one of [1] to [3], in which, in the general formulae (1) and (3a) to (3d), R1 represents an isopropyl group, R2, R3 and R4 each represent a hydrogen atom, and R5 and R6 are each a hydrogen atom;

[6] a process for producing a 2-alkenyl-3-aminothiophene derivative or a mixture thereof, in which a salt formed from a 3-aminothiophene derivative represented by the general formula (2) and an acid is reacted with a ketone derivative represented by the general formula (1);

[7] a process for producing a 2-alkenyl-3-aminothiophene derivative represented by any one of the general formulae (3a) to (3d) or a mixture thereof, in which the following steps (A) and (B) are conducted in the order of (A) and (B), Step (A): forming a salt from a 3-aminothiophene derivative represented by the general formula (2) and an acid; and Step (B): reacting the salt of a 3-aminothiophene derivative obtained in Step (A) with a ketone derivative represented by the general formula (1) for producing a 2-alkenyl-3-aminothiophene derivative or a mixture thereof;

[8] the process for producing a 2-alkenyl-3-aminothiophene derivative or a mixture thereof as set forth in [6] or [7], in which the reaction of the salt of a 3-aminothiophene derivative and the ketone derivative represented by the general formula (1) is carried out in the absence of a solvent;

[9] the process for producing a 2-alkenyl-3-aminothiophene derivative or a mixture thereof as set forth in [6] or [7], in which the reaction of the salt of a 3-aminothiophene derivative and the ketone derivative represented by the general formula (1) is carried out in a solvent;

[10] the process for producing a 2-alkenyl-3-aminothiophene derivative or a mixture thereof as set forth in any one of [6] or [9], in which, in the general formulae (2) and (3a) to (3d), R5 and R6 are each a hydrogen atom;

[11] the process for producing a 2-alkenyl-3-aminothiophene derivative or a mixture thereof as set forth in any one of [6] to [9], in which, in the general formulae (1) and (3a) to (3d), R1 represents an isopropyl group, R2, R3 and R4 each represent a hydrogen atom, and R5 and R6 are each a hydrogen atom;

[12] a process for producing a 2-alkenyl-3-aminothiophene derivative represented by any one of the general formulae (3'a) to (3'd) or a mixture thereof, in which a ketone derivative represented by the general formula (1) is reacted with a 3-aminothiophene derivative represented by the general formula (2'), which is obtained from methyl 3-aminothiophene-2-carboxylate as a starting material, in the presence of an acid catalyst,

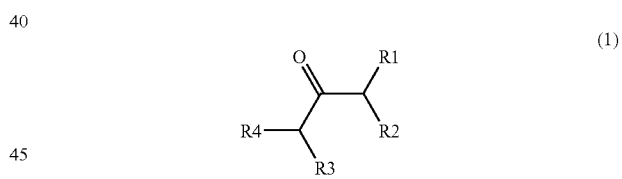

wherein, in the formula, R1, R2, R3 and R4 each independently represent a hydrogen atom, an alkyl group having 1 to 12 carbon atoms or an alkenyl group having 1 to 12 carbon atoms; at least one of R1, R2, R3 and R4 is an alkyl group having 1 to 12 carbon atoms or an alkenyl group having 1 to 12 carbon atoms; and R1 and R2, R1 and R3, R1 and R4, R2 and R3, R2 and R4, or R3 and R4 may be bonded with each other to form a cycloalkyl group,

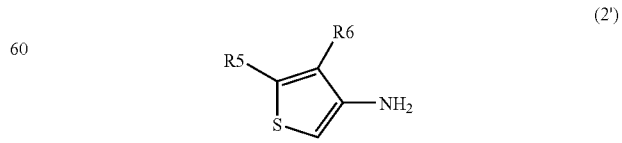

wherein, in the formula, both of R5 and R6 are hydrogen atoms,

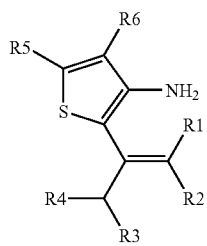 (3'a)

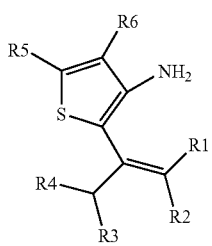 (3a)

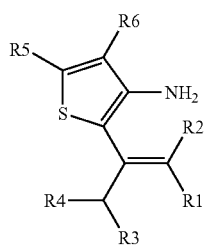 (3'b)

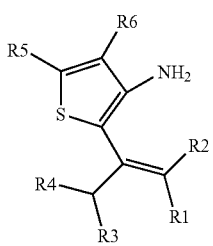 (3b)

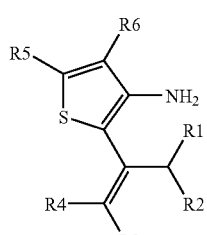 (3'c)

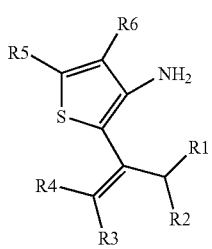 (3c)

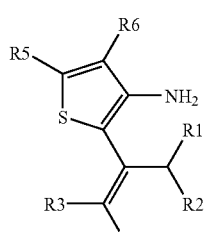 (3'd)

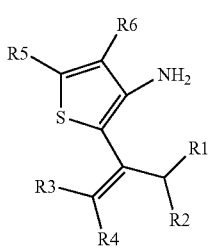 (3d)

wherein, in the formula, R1, R2, R3, R4, R5 and R6 are the same as those described above;

[13] the process for producing a 2-alkenyl-3-aminothiophene derivative or a mixture thereof as set forth in [12], in which the ketone derivative represented by the general formula (1) is reacted with the 3-aminothiophene derivative represented by the general formula (2') in the absence of a solvent;

[14] the process for producing a 2-alkenyl-3-aminothiophene derivative or a mixture thereof as set forth in [12], in which the ketone derivative represented by the general formula (1) is reacted with the 3-aminothiophene derivative represented by the general formula (2') in a solvent;

[15] the process for producing a 2-alkenyl-3-aminothiophene derivative or a mixture thereof as set forth in any one of [12] to [14], in which, in the general formula (1), R1 represents an isopropyl group, and R2, R3 and R4 are each a hydrogen atom, while, in the general formulae (3'a) to (3'd), R1 represents an isopropyl group, and R2, R3, R4, R5 and R6 are each a hydrogen atom;

[16] a 2-alkenyl-3-aminothiophene derivative represented by any one of the general formulae (3a) to (3d) and a mixture thereof, or a salt formed from said 2-alkenyl-3-aminothiophene derivative and an acid and a mixture thereof, wherein, in the formula, R1, R2, R3, R4, R5 and R6 are the same as those described above;

[17] the 2-alkenyl-3-aminothiophene derivative and the mixture thereof, or the salt formed from the 2-alkenyl-3-aminothiophene derivative and an acid and the mixture thereof as set forth in [16], in which, in the general formulae (3a) to (3d), R5 and R6 are each a hydrogen atom; and

[18] the 2-alkenyl-3-aminothiophene derivative and the mixture thereof, or the salt formed from the 2-alkenyl-3-aminothiophene derivative and an acid and the mixture thereof as set forth in [17], in which, in the general formulae (3a) to (3d), R1 represents an isopropyl group, and R2, R3 and R4 are each a hydrogen atom.

Alkenyl groups can be introduced into the 2-position of 3-aminothiophene derivatives by reacting 3-aminothiophene derivatives or salts thereof with various ketones without using as a protecting group for an amino group which are economically disadvantageous, and 2-alkenyl-3-aminothiophene derivatives, which are useful as intermediates for agricultural chemicals, can be produced in an industrially available method at low cost.

BEST MODE FOR CARRYING OUT THE INVENTION

The present invention will be described in more detail below.

In process for producing 2-alkenyl-3-aminothiophene derivatives represented by any one of the general formulae (3a) to (3d) or a mixture thereof, the substituent is not restricted to the following, but typical examples of the substituent include the following.

Namely, examples of the alkyl group having 1 to 12 carbon atoms include a methyl group, an ethyl group, an n-propyl group, an n-butyl group, an n-pentyl group, an n-hexyl group, an isopropyl group, an isobutyl group, a sec-butyl group, a tert-butyl group, a neopentyl group and the like. Examples of the halogen atom include a fluorine atom, a chlorine atom, a bromine atom, an iodine atom and the like. Examples of the alkenyl group having 1 to 12 carbon atoms include a vinyl group, a propenyl group, a butenyl group, a pentenyl group, a hexenyl group and the like. Examples of the alkynyl group having 1 to 12 carbon atoms include an ethynyl group, a propynyl group, a butynyl group, a pentynyl group, a hexynyl group and the like. Examples of the alkoxy group having 1 to 12 carbon atoms include a methoxy group, an ethoxy group and the like. Examples of the alkylthio group having 1 to 12 carbon atoms include a methylthio group, an ethylthio group and the like. Examples of the substituent of the alkyl group having 1 to 12 carbon atoms, the alkenyl group having 1 to 12 carbon atoms, the alkynyl group having 1 to 12 carbon atoms, the phenyl group or the hetero ring include alkyl groups such as a methyl group, an ethyl group, an isopropyl group, an isobutyl group and the like; alkenyl groups such as a vinyl group, a propenyl group and the like; alkynyl groups such as an ethynyl group, a propynyl group and the like; halogenated alkyl groups such as a trifluoromethyl group and the like; alkoxy groups such as a methoxy group, an ethoxy group and the like; halogen-substituted alkoxy groups such as a trifluoromethoxy group, a difluoromethoxy group and the like; alkylthio groups such a methylthio group, an ethylthio group and the like; alkylsulfinyl groups such as a methanesulfinyl group, an ethanesulfinyl group and the like; halogen-substituted alkylsulfinyl groups such as a trifluoromethanesulfinyl group, a difluoromethanesulfinyl group and the like; alkylsulfonyl groups such as a methanesulfonyl group, an ethanesulfonyl group and the like; halogen-substituted alkylsulfonyl groups such as a trifluoromethanesulfonyl group, a difluoromethanesulfonyl group and the like; phenyl groups, naphthyl groups, hetero rings such as furan, thiophene, oxazole, pyrrole, 1H-pyrazole, 3H-pyrazole, imidazole, thiazole, oxazole, isoxazole, isothiazole, tetrahydrofuran, pyrazolidine, pyridine, pyran, pyrimidine, pyrazine and the like; and halogen atoms such as a fluorine atom, a chlorine atom, a bromine atom, an iodine atom and the like.

The compounds represented by the general formulae (3a) to (3d) of the present invention are novel compounds, and can be produced from ketone derivatives represented by the general formula (1), and 3-aminothiophene derivatives represented by the general formula (2) or salts formed from the 3-aminothiophene derivatives and acids according to the method as described in the reaction formula (1).

Reaction Formula (1)

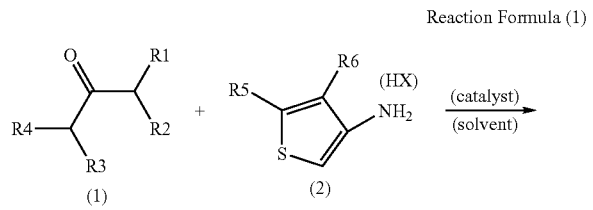

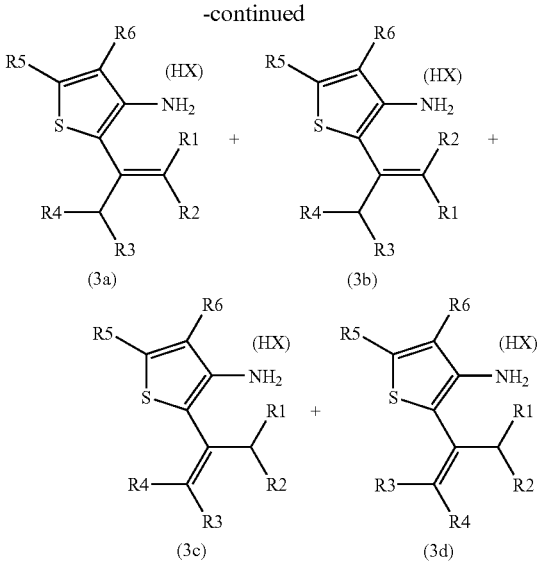

In the reaction formula (1), HX represents an acid capable of forming salts with 3-aminothiophene and/or 2-alkenyl-3-aminothiophene derivatives; R1, R2, R3 and R4 each independently represent a hydrogen atom, an alkyl group having 1 to 12 carbon atoms or an alkenyl group having 1 to 12 carbon atoms; at least one of R1, R2, R3 and R4 is an alkyl group having 1 to 12 carbon atoms or an alkenyl group having 1 to 12 carbon atoms; R1 and R2, R1 and R3, R1 and R4, R2 and R3, R2 and R4 or R3 and R4 may be bonded with each other to form a cycloalkyl group; R5 and R6 each independently represent a hydrogen atom, a halogen atom, a cyano group, a nitro group, an alkyl group having 1 to 12 carbon atoms, an alkenyl group having 1 to 12 carbon atoms, an alkynyl group having 1 to 12 carbon atoms, a phenyl group, a hetero ring, an alkoxy group having 1 to 12 carbon atoms or an alkylthio group having 1 to 12 carbon atoms; and R5 and R6 may be bonded with each other to form a cycloalkyl group.

In this reaction, a mixture of 2-alkenyl-3-aminothiophene derivatives represented by the general formulae (3a) to (3d) is obtained, and composed of the maximum 4 kinds of compounds. For example, when R1 to R4 of the substituents of ketone derivatives represented by the general formula (1) are all different, a product is a mixture composed of four kinds of compounds, when a ketone derivative represented by the general formula (1) is 4-methyl-2-pentanone, a product is a mixture composed of three kinds of compounds, or when a ketone derivative represented by the general formula (1) is cyclohexanone, a product is a single compound. These mixtures can be isolated by using a means of chromatography or the like, and can be used as intermediates either in the form of a single compound or a mixture.

In the reaction formula (1), 2-alkenyl-3-aminothiophene derivatives represented by the general formulae (3a) to (3d) can be produced by reacting 3-aminothiophene derivatives represented by the general formula (2) with ketone derivatives represented by the general formula (1) in the absence of a solvent or in a solvent, in the presence of an acid catalyst. Furthermore, 2-alkenyl-3-aminothiophene derivatives represented by the general formulae (3a) to (3d) can be produced by reacting salts formed from 3-aminothiophene derivatives represented by the general formula (2) and acids HX with ketone derivatives represented by the general formula (1) in the absence of a solvent or in a solvent.

The amount of ketone derivatives represented by the general formula (1) used is preferably not less than 1 mole equivalent based on the 3-aminothiophene derivatives represented by the general formula (2) or salts thereof in use, and ketone derivatives can also be used as a solvent.

The acid catalyst represented by the reaction formula (1) used for the reaction is not restricted to the following, but typical examples include inorganic acids such as hydrogen chloride, hydrogen bromide, hydrochloric acid solution, sulfuric acid, nitric acid, phosphoric acid and the like; organic acids such as trifluoroacetic acid, cyanoacetic acid, benzoic acid, 4-cyanobenzoic acid, 2-chlorobenzoic acid, 2-nitrobenzoic acid, citric acid, fumaric acid, malonic acid, oxalic acid, maleic acid, phenoxyacetic acid, methanesulfonic acid, p-toluenesulfonic acid, benzenesulfonic acid, p-toluenesulfinic acid and the like; Lewis acids such as zinc chloride, aluminum chloride and the like; solid acids such as zeolite and the like; ion exchange resins and the like.

These acid catalysts can be used singly, or two or more different acids can be used at the same time.

The amount of the acid catalyst used is preferably not less than 0.2 N equivalent and further preferably from 1.0 to 3.0 N equivalents, based on the 3-aminothiophene derivatives represented by the general formula (2) in use. When expressing in terms of the mole equivalent number, for example, the amount is preferably not less than 0.2 mole equivalent and further preferably from 1.0 to 5.0 mole equivalents, based on the monovalent acid, while it is preferably not less than 0.1 mole equivalent and further preferably from 0.5 to 2.5 mole equivalents, based on the divalent acid.

The acid forming salts with 3-aminothiophene derivatives represented by the general formula (2) or 2-alkenyl-3-aminothiophene derivatives represented by the general formulae (3a) to (3d) are not restricted to the following, but typical examples include inorganic acids such as hydrogen chloride, hydrogen bromide, sulfuric acid, nitric acid, phosphoric acid and the like; and organic acids such as trifluoroacetic acid, cyanoacetic acid, benzoic acid, 4-cyanobenzoic acid, 2-chlorobenzoic acid, 2-nitrobenzoic acid, citric acid, fumaric acid, malonic acid, oxalic acid, maleic acid, phenoxyacetic acid, methanesulfonic acid, p-toluenesulfonic acid, benzenesulfonic acid, p-toluenesulfinic acid and the like.

The amount of the acid for forming salts with 3-aminothiophene derivatives represented by the general formula (2) or 2-alkenyl-3-aminothiophene derivatives represented by the general formulae (3a) to (3d) is not particularly limited. However, the amount of the monovalent acid is preferably not less than 1.0 mole equivalent based on the 3-aminothiophene derivatives represented by the general formula (2), while the multivalent acid is preferably not less than the theoretical equivalent for forming salts with 3-aminothiophene derivatives represented by the general formula (2).

An acid identical to or different from the acid constituting a salts can be added to the above salts of 3-aminothiophene derivatives for the reaction. The acid catalyst to be added can be used singly, or two or more different acids can be used at the same time.

The amount of the acid catalyst added is not particularly limited, but it is further preferably from 0.1 to 4.0 N equivalents based on the salts of the 3-aminothiophene derivatives represented by the general formula (2) in use.

Examples of the solvent used for the reaction include alcohol solvents such as methanol, ethanol, propanol, butanol and the like; halogenated hydrocarbon solvents such as dichloromethane, chloroform and the like; aromatic hydrocarbon solvents such as benzene, toluene, xylene and the like; aliphatic hydrocarbon solvents such as hexane, heptane and the like; aliphatic ester solvents such as ethyl acetate, butyl acetate and the like; polar aprotic solvents such as dimethylformamide, dimethylacetamide, dimethyl sulfoxide, 1,3-dimethyl-2-imidazolidinone, 1-methyl-2-pyrrolidone and the like; ether solvents such as ethyl ether, isopropyl ether, 1,2-dimethoxyethane, tetrahydrofuran, dioxane and the like; and nitrile solvents such as acetonitrile, propionitrile and the like. A mixed solvent thereof can be used. Furthermore, the reaction can also be carried out without a solvent.

The amount of the solvent used is not particularly limited, but the concentration of the 3-aminothiophene derivatives represented by the general formula (2) is usually not less than 0.1 weight % and preferably from 1 to 50 weight %.

The reaction temperature and the reaction time in the above reaction can be varied in a wide range. In general, the reaction temperature is preferably −78 to 300 degree centigrade and more preferably from 0 to 150 degree centigrade, while the reaction time is preferably from 0.01 to 100 hours and more preferably from 1 to 50 hours.

Furthermore, in this reaction, with the progress of the reaction, water is generated along with the compound represented by the general formulae (3a) to (3d), but the reaction can be accelerated by removing generated water if necessary. A method to remove water is not restricted to the following, but examples thereof include a method for adding a dehydrating agent such as anhydrous magnesium sulfate, anhydrous sodium sulfate, molecular sieves or the like, and a method such as azeotropic dehydration or the like.

The reaction temperature in the reaction must be set to a reaction temperature capable of proceeding the reaction, while the acid used as a catalyst or salt formation must also be used by properly selecting an acid capable of proceeding the reaction. When a solvent is used for the reaction, a solvent which can be used without any problem at the reaction temperature capable of proceeding the reaction can be properly selected and used.

2-alkenyl-3-aminothiophene derivatives represented by the compound represented by the general formulae (3a) to (3d) obtained by the reaction and a mixture thereof, or salts formed from the aforementioned 2-alkenyl-3-aminothiophene derivatives and acids, and a mixture thereof are a mixture composed of novel compounds,

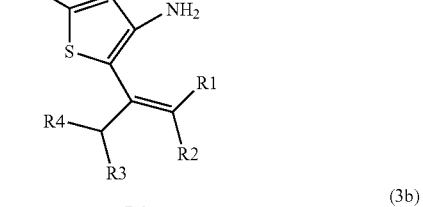

(3a)

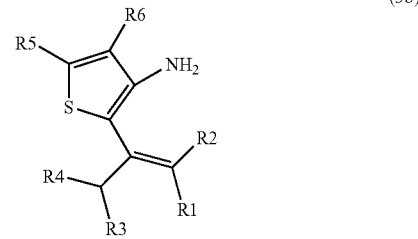

(3b)

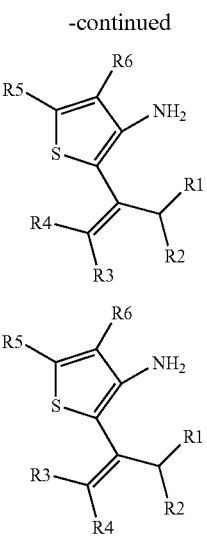

wherein, in the formula, R1, R2, R3 and R4 each independently represent a hydrogen atom, an alkyl group having 1 to 12 carbon atoms or an alkenyl group having 1 to 12 carbon atoms; at least one of R1, R2, R3 and R4 is an alkyl group having 1 to 12 carbon atoms or an alkenyl group having 1 to 12 carbon atoms; R1 and R2, R1 and R3, R1 and R4, R2 and R3, R2 and R4, or R3 and R4 may be bonded with each other to form a cycloalkyl group; R5 and R6 are each independently a hydrogen atom, a halogen atom, a cyano group, a nitro group, an alkyl group having 1 to 12 carbon atoms, an alkenyl group having 1 to 12 carbon atoms, an alkynyl group having 1 to 12 carbon atoms, a phenyl group, a hetero ring, an alkoxy group having 1 to 12 carbon atoms or an alkylthio group having 1 to 12 carbon atoms; and R5 and R6 may be bonded with each other to form a cycloalkyl group.

EXAMPLES

The present invention is now illustrated in detail below with reference to Examples and Test Examples. However, the present invention is not restricted to these Examples.

Example 1

Synthesis Example of Toluene Solution of 3-aminothiophene

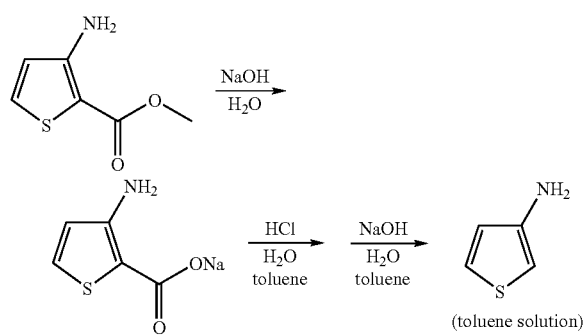

A 32% aqueous sodium hydroxide solution (150.0 g, 1.2 mol) and water (250.0 g) were mixed, methyl 3-aminothiophene-2-carboxylate (170.0 g, 1.1 mol) was added thereinto at room temperature, and the resulting solution was stirred at 70 degree centigrade for 3 hours. The reaction solution was cooled to room temperature, toluene (889.0 g) was added thereinto, and then 35% hydrochloric acid (259.2 g, 2.5 mol) was added dropwise thereto while maintaining the temperature of the reaction solution at 20 to 25 degree centigrade under a nitrogen atmosphere for adjusting the reaction solution to the acidic side. The dropwise addition was carried out over 1.5 hours while paying attention to the reaction temperature and carbon dioxide to be generated, and after the completion of dropwise addition, the solution was further stirred for 1.5 hours. The reaction solution was cooled to not more than 10 degree centigrade, and then the reaction solution was adjusted to the alkaline side using a 32% aqueous sodium hydroxide solution. The organic layer was separated, and then dried over anhydrous sodium sulfate. The inorganic salt was filtered, and then washed with toluene to give 759.2 g of a toluene solution of a desired 3-aminothiophene (3-aminothiophene: concentration; 12.8 weight %, content; 97.5 g, yield; 86%).

Example 2

Reaction of 3-aminothiophene with 4-methyl-2-pentanone

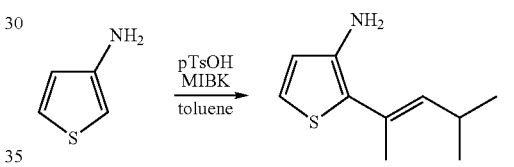

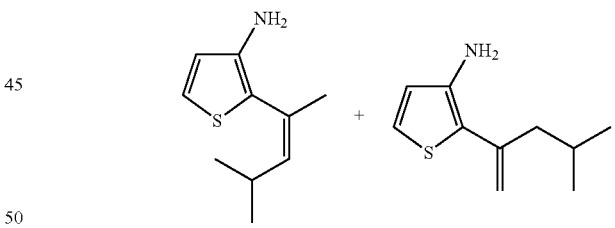

Into a solution obtained by dissolving 3-aminothiophene (2.5 g, 25.2 mmol) in toluene (85.0 g), which was obtained by the method in Example 1 using methyl 3-aminothiophene-2-carboxylate as a starting material were added p-toluenesulfonic acid (0.2 g, 1.1 mmol) and 4-methyl-2-pentanone (100.0 g, 998.4 mmol) at room temperature, and the resulting solution was stirred under reflux under nitrogen atmosphere for 2 hours. The reaction solution was cooled to room temperature, and then washed with a 10% aqueous sodium hydroxide solution two times, and the obtained organic layer was concentrated under reduced pressure to give an oily substance. The resulting concentrate was purified by silica gel column chromatography to give 0.9 g of an oily substance as a mixture of three compounds including 3-amino-2-{(E)-(4-methyl-2-penten-2-yl)}thiophene, 3-amino-2-{(Z)-(4-methyl-2-penten-2-yl)}thiophene and 3-amino-2-(4-methyl-1-penten-2-yl)thiophene (yield: 19%).

Example 3

Reaction of 3-aminothiophene with 4-methyl-2-pentanone

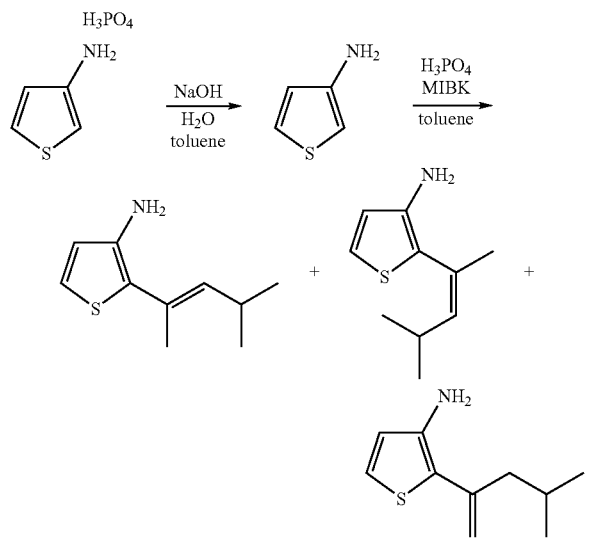

3-aminothiophene phosphate (5.0 g, 16.1 mmol) was added into water (100 g) in an ice water bath for dissolving. Toluene (50.0 g) was added in an ice water bath, and then a 10% aqueous sodium hydroxide solution was added under stirring in an ice water bath for adjusting the reaction solution to the alkaline side. The organic layer was separated, and then the aqueous layer was further extracted with toluene. To the toluene solution of 3-aminothiophene obtained as described above were added 85% phosphoric acid (0.9 g, 8.1 mmol) and 4-methyl-2-pentanone (50.0 g, 499.2 mmol) at room temperature, and the resulting solution was stirred under reflux under nitrogen atmosphere for 5 hours with removing water. The reaction solution was cooled to room temperature, and then washed with a 10% aqueous sodium hydroxide solution two times, and the obtained organic layer was concentrated under reduced pressure to give an oily substance. The resulting concentrate was purified by silica gel column chromatography to give 1.0 g of an oily substance as a mixture of three compounds including 3-amino-2-{(E)-(4-methyl-2-penten-2-yl)}thiophene, 3-amino-2-{(Z)-(4-methyl-2-penten-2-yl)}thiophene and 3-amino-2-(4-methyl-1-penten-2-yl)thiophene (yield: 34%).

Example 4

Synthesis Example of 3-aminothiophene Phosphate

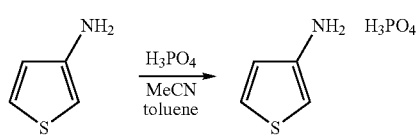

While a solution obtained by mixing 85% phosphoric acid (143.6 g, 1.2 mol) and acetonitrile (500.0 g) was cooled to not more than 15 degree centigrade and stirred under nitrogen atmosphere, a toluene solution (847.3 g, 3-aminothiophene: concentration; 13.1 weight %, content; 111.0 g, 1.1 mol) of 3-aminothiophene prepared in the same manner as in Example 1 was added dropwise thereto. The precipitated crystal was filtered and washed with acetonitrile (200.0 g). The obtained crystal was suspended in acetonitrile (800.0 g) and stirred in an ice water bath for 1 hour. The crystal was filtered again and washed with acetonitrile (200.0 g). The resulting crystal was dried under reduced pressure to give 148.5 g of 3-aminothiophene phosphate (yield: 68%).

Example 5

Synthesis Example of 3-aminothiophene ½ Oxalate

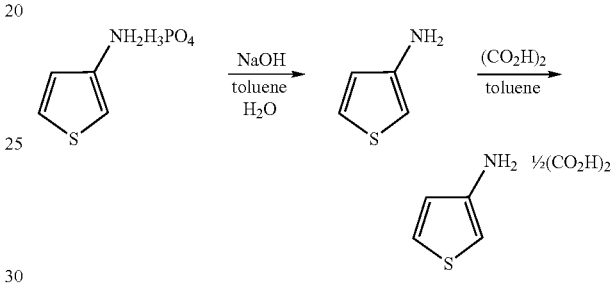

3-aminothiophene phosphate (30.0 g, 152.2 mmol) was dissolved in water (600.0 g) in an ice water bath, and toluene (400.0 g) was added thereto. The reaction solution was adjusted to the alkaline side with a 32% aqueous sodium hydroxide solution while stirring under nitrogen atmosphere and maintaining the reaction temperature at not more than 5 degree centigrade. The organic layer was separated, and then the aqueous layer was extracted with toluene (100.0 g) again. The combined organic layer was extracted with water (200.0 g) and dried over anhydrous sodium sulfate. The inorganic salt was filtered and then washed with toluene to give 567.2 g of a toluene solution of 3-aminothiophene (3-aminothiophene: concentration; 2.3 weight %, content; 12.8 g, 129.4 mmol). The obtained solution was cooled to 5 degree centigrade, oxalic acid dihydrate (9.0 g, 71.2 mmol) was added thereto, and the resulting mixture was stirred for 1 hour. The generated crystal was collected and then washed with ethanol (100.0 g). The obtained wet crystal was dried under reduced pressure to give 15.6 g of 3-aminothiophene ½ oxalate as a white crystal (yield: 71%).

Example 6

Synthesis Example of 3-aminothiophenebenzene Sulfonate

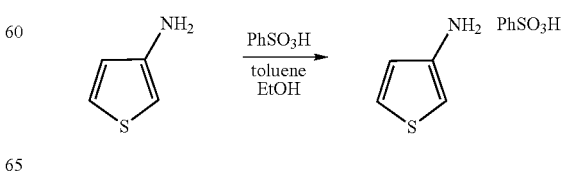

666.4 g of a toluene solution of 3-aminothiophene prepared in the same manner as in Example 1 (3-aminothiophene:

concentration; 12.8 weight %, content; 85.3 g, 0.86 mol) was cooled to not more than 5 degree centigrade, and a solution obtained by dissolving benzenesulfonic acid monohydrate (152.2 g, 0.95 mol) in ethanol (200 g) was added dropwise while stirring under nitrogen atmosphere. The resulting solution was stirred for 1 hour. The generated crystal was collected and washed with toluene (100 g). The obtained wet crystal was dried under reduced pressure to give 154.9 g of 3-aminothiophenebenzene sulfonate as a light pink crystal (yield: 70%).

Example 7

Synthesis Example of 3-aminothiophene Hydrochloride

655.0 g of a 4-methyl-2-pentanone solution of 3-aminothiophene prepared in the same manner as in Example 14 (3-aminothiophene: concentration; 5.8 weight %, content; 37.9 g, 0.38 mol) was cooled to not more than 5 degree centigrade, a 4N hydrogen chloride-ethyl acetate solution (105.0 ml, 0.42 mol) was added dropwise while stirring under nitrogen atmosphere. The resulting solution was stirred for 1 hour. The generated crystal was collected, washed with acetonitrile (200 ml), and recrystallized with methanol and diisopropyl ether. The obtained wet crystal was dried under reduced pressure to give 33.5 g of 3-aminothiophene hydrochloride as a light pink crystal (yield: 58%).

Example 8

Reaction of 3-aminothiophene ½ Oxalate with 4-methyl-2-pentanone

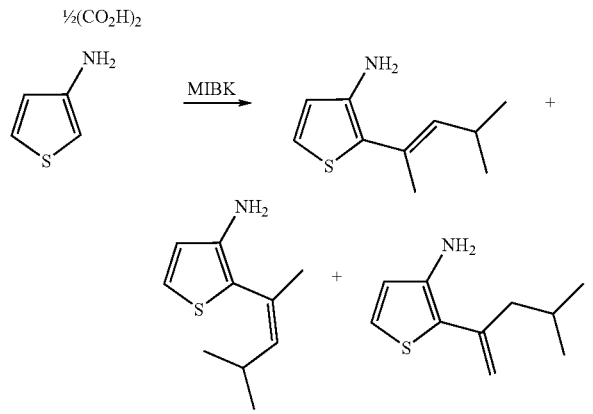

3-aminothiophene ½ oxalate (1.0 g, 6.9 mmol) was added to 4-methyl-2-pentanone (122.1 g) and reacted at 90 degree centigrade for 2 hours. The reaction mixture in a suspended state at the beginning became a solution state after 2 hours. As a result of the analysis by the HPLC internal standard method of the reaction solution, 0.7 g was produced as a mixture of three compounds including 3-amino-2-{(E)-(4-methyl-2-penten-2-yl)}thiophene, 3-amino-2-{(Z)-(4-methyl-2-penten-2-yl)}thiophene and 3-amino-2-(4-methyl-1-penten-2-yl)thiophene (yield: 54%).

Example 9

Reaction of 3-aminothiophenebenzene Sulfonate with 4-methyl-2-pentanone

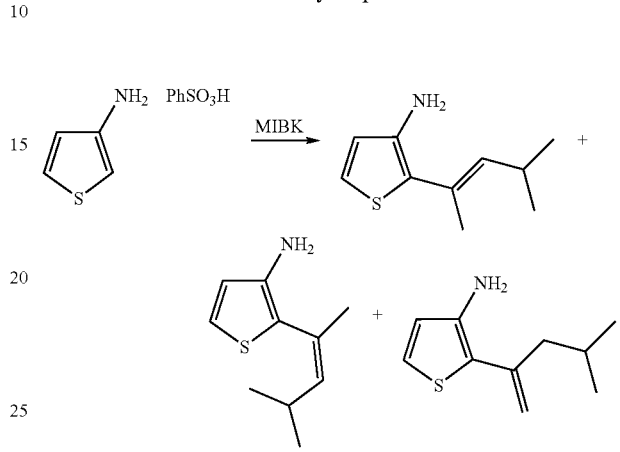

3-aminothiophenebenzene sulfonate (2.1 g, 7.7 mmol, purity: 91.6%) was added to 4-methyl-2-pentanone (121.2 g) and reacted at 60 degree centigrade for 8 hours. The reaction mixture in a suspended state at the beginning became a solution state after 6 hours. As a result of the analysis by the HPLC internal standard method of the reaction solution, 1.3 g was produced as a mixture of three compounds including 3-amino-2-{(E)-(4-methyl-2-penten-2-yl)}thiophene, 3-amino-2-{(Z)-(4-methyl-2-penten-2-yl)}thiophene and 3-amino-2-(4-methyl-1-penten-2-yl)thiophene was produced (yield: 96%).

Example 10

Reaction of 3-aminothiophenebenzene Sulfonate with 4-methyl-2-pentanone

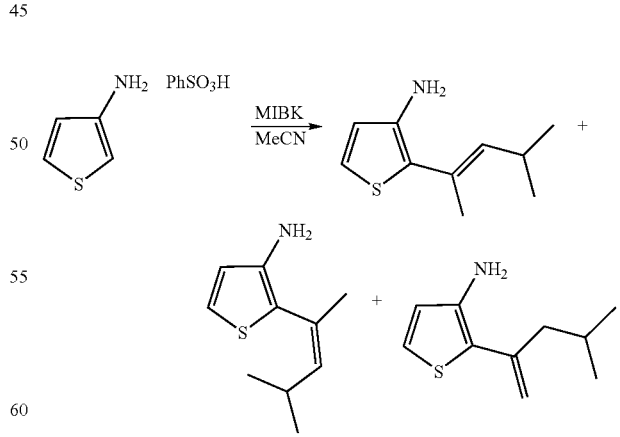

3-aminothiophenebenzene sulfonate (5.0 g, 17.9 mmol, purity: 91.6%) was added to 4-methyl-2-pentanone (45.2 g) and acetonitrile (50.0 g), and reacted at 60 degree centigrade for 8 hours. As a result of the analysis by the HPLC internal standard method of the reaction solution, 1.9 g was produced as a mixture of three compounds including 3-amino-2-{(E)-(4-methyl-2-penten-2-yl)}thiophene, 3-amino-2-{(Z)-(4-methyl-2-penten-2-yl)}thiophene and 3-amino-2-(4-methyl-1-penten-2-yl)thiophene (yield: 60%).

Example 11

Reaction of 3-aminothiophenebenzene Sulfonate with 4-methyl-2-pentanone

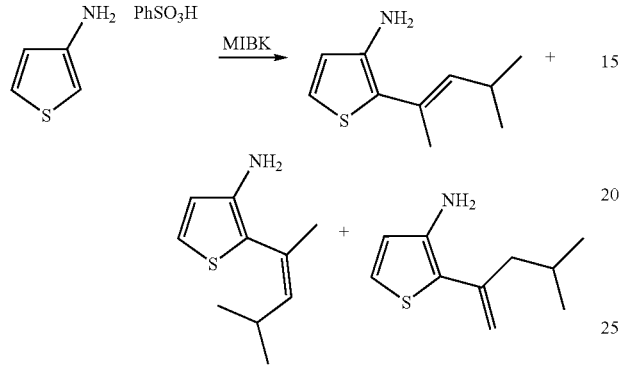

3-aminothiophenebenzene sulfonate (21.0 g, 81.6 mmol) was added to 4-methyl-2-pentanone (1251.6 g, 12.5 mol) and the resulting mixture was stirred under nitrogen atmosphere at 65 degree centigrade for 7 hours. The reaction solution was cooled to room temperature, and then washed with a 10% aqueous sodium hydroxide solution two times. The resulting organic layer was purified by vacuum distillation to give 11.8 g of an oily substance as a mixture of three compounds including 3-amino-2-{(E)-(4-methyl-2-penten-2-yl)}thiophene, 3-amino-2-{(Z)-(4-methyl-2-penten-2-yl)}thiophene and 3-amino-2-(4-methyl-1-penten-2-yl)thiophene (yield: 80%, boiling point: 98 to 108 degree centigrade/4 mmHg).

Example 12

Reaction of 3-aminothiophene Hydrochloride with 4-methyl-2-pentanone

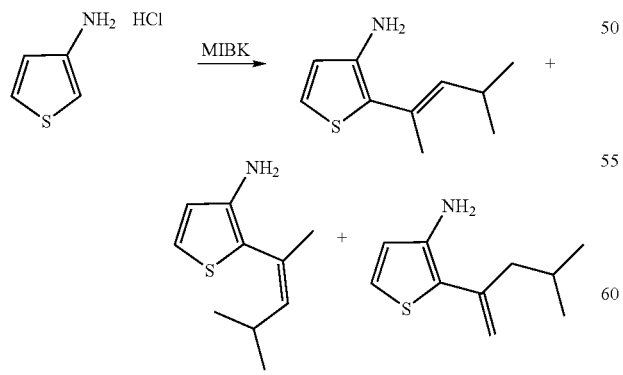

3-aminothiophene hydrochloride (3.0 g, 19.6 mmol, purity: 89.3%) was added to 4-methyl-2-pentanone (97.0 g) and reacted at 60 degree centigrade for 17 hours. As a result of the analysis by the HPLC internal standard method of the reaction solution, 2.5 g was produced as a mixture of three compounds including 3-amino-2-{(E)-(4-methyl-2-penten-2-yl)}thiophene, 3-amino-2-{(Z)-(4-methyl-2-penten-2-yl)}thiophene and 3-amino-2-(4-methyl-1-penten-2-yl)thiophene (yield: 71%).

Example 13

Reaction of 3-aminothiophenebenzene Sulfonate with 4-methyl-2-pentanone

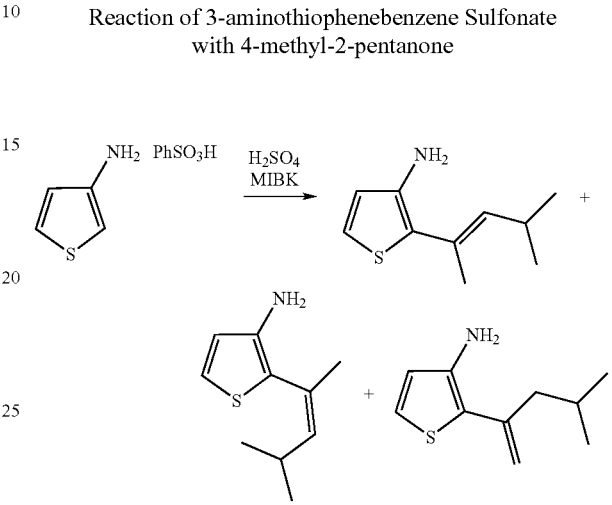

3-aminothiophenebenzene sulfonate (2.0 g, 7.1 mmol, purity: 91.4%) was added to 4-methyl-2-pentanone (138.4 g), and 95% sulfuric acid (0.4 g, 3.6 mmol) was added dropwise thereto at room temperature. The resulting reaction solution was stirred under nitrogen atmosphere at 60 degree centigrade for 6 hours. The reaction solution was cooled to room temperature, and then washed with a 10% aqueous sodium hydroxide solution, and separated. As a result of the analysis by the HPLC internal standard method of the obtained organic layer, 1.1 g was obtained as a mixture of three compounds including 3-amino-2-{(E)-(4-methyl-2-penten-2-yl)}thiophene, 3-amino-2-{(Z)-(4-methyl-2-penten-2-yl)}thiophene and 3-amino-2-(4-methyl-1-penten-2-yl)thiophene (yield: 83%).

Example 14

Synthesis Example of 4-methyl-2-pentanone Solution of 3-aminothiophene

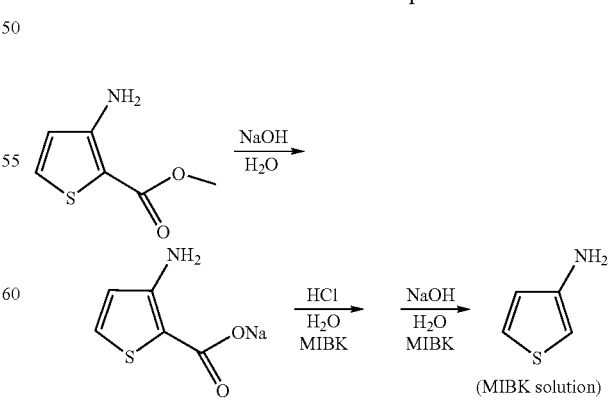

A 32% aqueous sodium hydroxide solution (77.2 g, 0.6 mol) and water (246.0 g) were mixed, and methyl 3-aminothiophene-2-carboxylate (80.0 g, 0.5 mol) was added thereinto at room temperature, and the resulting solution was reacted at 70 degree centigrade for 3 hours. The reaction solution was cooled to room temperature, 4-methyl-2-pentanone (321.5 g) was added thereinto, and then 35% hydrochloric acid (118.1 g, 1.2 mol) was added dropwise thereto while maintaining the temperature of the reaction solution at 20 to 25 degree centigrade under a nitrogen stream for adjusting the reaction solution to the acidic side. The dropwise addition was carried out over 1.5 hours while paying attention to the reaction temperature and carbon dioxide to be generated, and after the completion of dropwise addition, the solution was further stirred for 2 hours. The reaction solution was cooled to 5 degree centigrade, and then the reaction solution was adjusted to the alkaline side using a 32% aqueous sodium hydroxide solution. The organic layer was separated, and then the aqueous layer was extracted with 4-methyl-2-pentanone (321.5 g) again. The obtained organic layer was mixed with the previously obtained organic layer to give 671.2 g of an desired 4-methyl-2-pentanone solution of 3-aminothiophene (3-aminothiophene: concentration; 6.3 weight %, content; 42.1 g, yield: 85%).

Example 15

Reaction of 3-aminothiophene with 4-methyl-2-pentanone

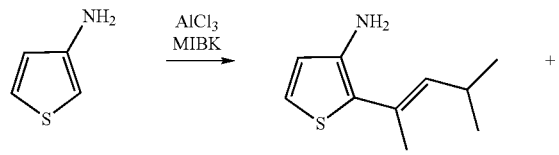

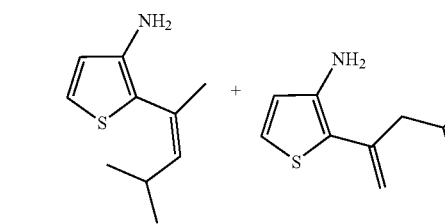

Into a solution obtained by dissolving 3-aminothiophene (2.0 g, 20.6 mmol) in 4-methyl-2-pentanone (28.3 g), which was obtained by the method in Example 14 using methyl 3-aminothiophene-2-carboxylate as a starting material was added aluminum chloride (1.3 g, 24.5 mmol) at room temperature, and the resulting solution was stirred under nitrogen atmosphere at 60 degree centigrade for 5 hours. The reaction solution was cooled to room temperature, and then washed with a 10% aqueous sodium hydroxide solution, and separated. As a result of the analysis by the HPLC internal standard method of the obtained organic layer, 0.4 g was produced as a mixture of three compounds including 3-amino-2-{(E)-(4-methyl-2-penten-2-yl)}thiophene, 3-amino-2-{(Z)-(4-methyl-2-penten-2-yl)}thiophene and 3-amino-2-(4-methyl-1-penten-2-yl)thiophene (yield: 12%).

Example 16

Reaction of 3-aminothiophene with 4-methyl-2-pentanone

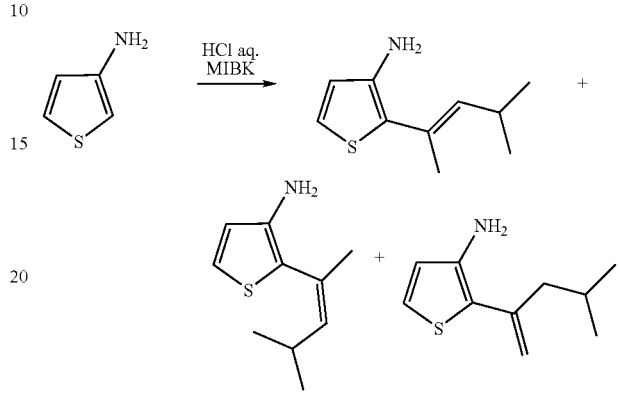

Into a solution obtained by dissolving 3-aminothiophene (1.8 g, 18.1 mmol) in 4-methyl-2-pentanone (30.1 g), which was obtained in the same manner as in Example 14 using methyl 3-aminothiophene-2-carboxylate as a starting material was added concentrated hydrochloric acid (9.3 g, 90.5 mmol) at room temperature, and the resulting solution was stirred under nitrogen atmosphere at 60 degree centigrade for 5 hours. The reaction solution was cooled to room temperature, and then washed with a 10% aqueous sodium hydroxide solution, and separated. As a result of the analysis by the HPLC internal standard method of the obtained organic layer, 0.5 g was produced as a mixture of three compounds including 3-amino-2-{(E)-(4-methyl-2-penten-2-yl)}thiophene, 3-amino-2-{(Z)-(4-methyl-2-penten-2-yl)}thiophene and 3-amino-2-(4-methyl-1-penten-2-yl)thiophene (yield: 14%).

Example 17

Reaction of 3-aminothiophene with 4-methyl-2-pentanone

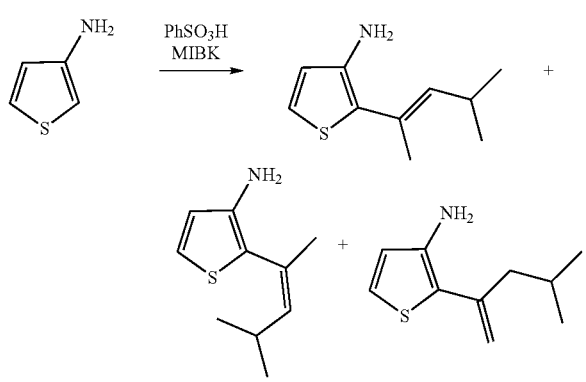

Into a solution obtained by dissolving 3-aminothiophene (2.0 g, 20.4 mmol) in 4-methyl-2-pentanone (30.0 g), which was obtained in the same manner as in Example 14 using methyl 3-aminothiophene-2-carboxylate as a starting material was added anhydrous benzenesulfonic acid (3.9 g, 24.5 mmol) at room temperature, and the resulting solution was stirred under nitrogen atmosphere at 60 degree centigrade for 15 hours. The reaction solution was cooled to room temperature, and then washed with a 10% aqueous sodium hydroxide solution, and separated. As a result of the analysis by the HPLC internal standard method of the obtained organic layer, 2.4 g was produced as a mixture of three compounds including 3-amino-2-{(E)-(4-methyl-2-penten-2-yl)}thiophene, 3-amino-2-{(Z)-(4-methyl-2-penten-2-yl)}thiophene and 3-amino-2-(4-methyl-1-penten-2-yl)thiophene (yield: 65%).

Example 18

Reaction of 3-aminothiophene with 4-methyl-2-pentanone

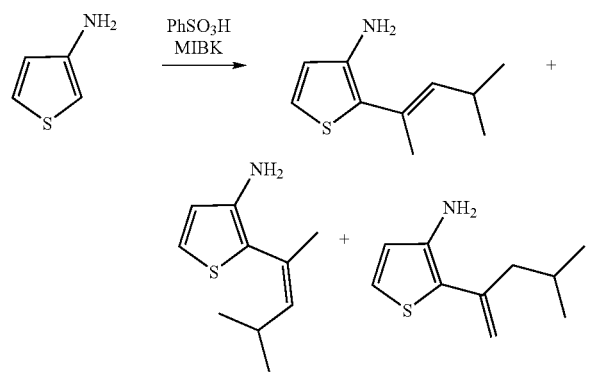

Into a solution obtained by dissolving 3-aminothiophene (1.4 g, 14.5 mmol) in 4-methyl-2-pentanone (30.0 g), which was obtained in the same manner as in Example 14 using methyl 3-aminothiophene-2-carboxylate as a starting material was added anhydrous benzenesulfonic acid (4.7 g, 29.7 mmol) at room temperature, and the resulting solution was stirred under nitrogen atmosphere at 60 degree centigrade for 30 hours. The reaction solution was cooled to room temperature, and then washed with a 10% aqueous sodium hydroxide solution, and separated. As a result of the analysis by the HPLC internal standard method of the obtained organic layer, 2.1 g was produced as a mixture of three compounds including 3-amino-2-{(E)-(4-methyl-2-penten-2-yl)}thiophene, 3-amino-2-{(Z)-(4-methyl-2-penten-2-yl)}thiophene and 3-amino-2-(4-methyl-1-penten-2-yl)thiophene (yield: 80%).

Example 19

Reaction of 3-aminothiophene with 4-methyl-2-pentanone

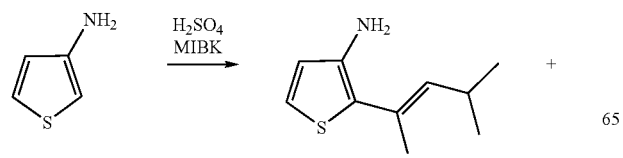

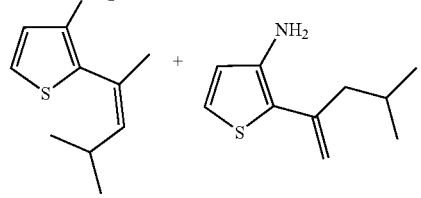

95% Sulfuric acid (0.4 g, 3.9 mol) was added to a 0.5% 4-methyl-2-pentanone solution (30.0 g, 1.5 mmol) of 3-aminothiophene obtained by diluting a 4-methyl-2-pentanone solution of 3-aminothiophene, which was obtained in the same manner as in Example 14 using methyl-3-aminothiophene-2-carboxylate as a starting material at room temperature, and the resulting solution was stirred under nitrogen atmosphere at 60 degree centigrade for 6 hours. The reaction solution was cooled to room temperature, and then washed with a 10% aqueous sodium hydroxide solution, and separated. As a result of the analysis by the HPLC internal standard method of the obtained organic layer, 0.2 g was produced as a mixture of three compounds including 3-amino-2-{(E)-(4-methyl-2-penten-2-yl)}thiophene, 3-amino-2-{(Z)-(4-methyl-2-penten-2-yl)}thiophene and 3-amino-2-(4-methyl-1-penten-2-yl)thiophene (yield: 76%).

Examples of the compound represented by the general formulae (3a) to (3d) of the present invention were illustrated in Table 1 below.

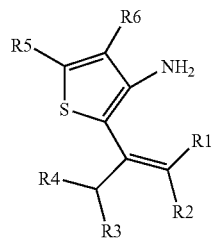

(3a)

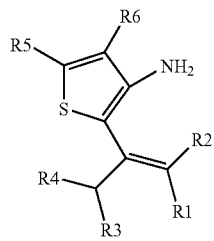

(3b)

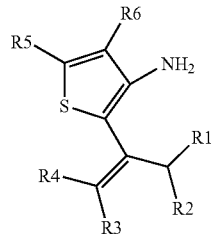

(3c)

-continued
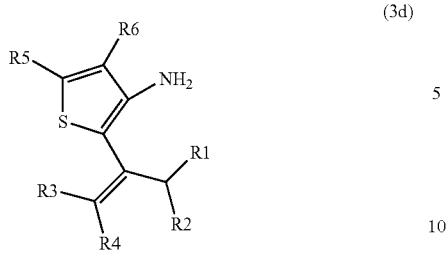
(3d)
TABLE 1
Physical Properties of Compounds (3a) to (3d)
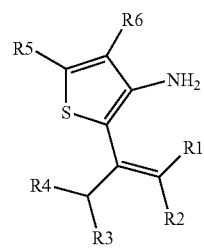
(3a)
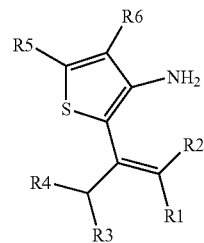
(3b)
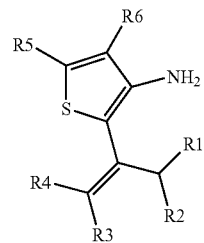
(3c)
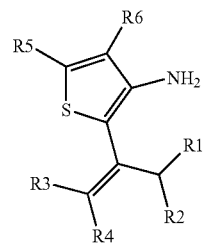
(3d)
| No. | Structure | Physical properties |
|---|---|---|
| 1 | In 3a, 3b, 3c (= 3d), three kinds of isomer mixtures of R1 = isopropyl and R2 = R3 = R4 = R5 = R6 = H | Colorless oil b.p. 98-108° C./4 mmHg $^1$H-NMR · (CDCl$_3$): 0.94 (6 × $^2$/$_3$H, d, J = 6.8 Hz), 1.04 (3 × $^1$/$_3$H, d, J = 6.8 Hz), 1.94 (3 × $^2$/$_3$H, s), 2.00 (3 × $^1$/$_3$H), 2.41 (1 × $^2$/$_3$H, q, J = 6.8 Hz), 2.65-2.71 (1 × $^1$/$_3$H, m), 3.41 (2H, brs), 5.43 |

TABLE 1-continued

| | | |
|---|---|---|
| | | (1 × ⅔H, d, J = 9.8 Hz), 5.44-5.45 (1 × ⅓H, m), 6.57 (1 × ⅓H, d, J = 5.4 Hz), 6.58 (1 × ⅔H, d, J = 5.4 Hz), 6.98 (1 × ⅓H, d, J = 5.4 Hz), 7.05 (1 × ⅔H, d, J = 5.4 Hz). Other signals in lc (= 1d) are difficult to be distinguished because they overlap with other peaks, but 2H at the end of a double bond show an integrated intensity of about 1/10 of 2.00 observed in a range of 5.11 to 5.15. |
| 2 | In structural formula 3a, a single product of R1 = isopropyl and R2 = R3 = R4 = R5 = R6 = H | Colorless oil <br> ¹H-NNR · (CDCl₃) 1.04 (3H, d, J = 6.8 Hz), 2.00 (3H, s), 2.65-2.71 (1H, m), 3.41 (2H, brs), 5.44-5.45 (1H, m), 6.57 (1H, d, J = 5.4 Hz), 6.98 (1H, d, J = 5.4 Hz). |
| 3 | In structural formula 3b, a single product of R1 = isopropyl and R2 = R3 = R4 = R5 = R6 = H | Colorless oil b.p. 122-124° C./8 mmHg <br> ¹H-NMR · (CDCl₃): 0.94 (6H, d, J = 6.8 Hz), 1.94 (3H, s), 2.41 (1H, q, J = 6.8 Hz), 3.41 (2H, brs), 5.43 (1H, d, J = 9.8 Hz), 6.58 (1H, d, J = 5.4 Hz), 7.05 (1H, d, J = 5.4 Hz) |
| 4 | In structural formula 3c (= 3d), a single product of R1 = isopropyl and R2 = R3 = R4 = R5 = R6 = H | Colorless oil <br> ¹H-NMR · (CDCl₃) 0.92 (3H, d, J = 6.8 Hz), 1.75-1.78 (1H, m), 2.07-2.15 (1H, m), 3.43 (2R, brs), 5.1-15.15 (1H, m), 6.52 (1H, d, J = 5.4 Hz), 7.01 (1H, d, J = 5.4 Hz). |
| 5 | Phosphate of a compound of R1 = isopropyl and R2 = R3 = R4 = R5 = R6 = H | White crystal <br> ¹H-NMR · (DMSOd₆): 0.99 (6H, d, J = 6.8 Hz), 1.94 (3H, s), 2.63 (1H, g, J = 6.8 Hz), 4.21 (2H, brs), 5.36-5.38 (1H, m), 6.55 (1H, d, J = 5.4 Hz), 7.05 (1H, d, J = 5.4 Hz). |

The invention claimed is:

1. A process for producing a 2-alkenyl-3-aminothiophene derivative of formulae (3a) to (3d) or a mixture thereof, in which a ketone derivative of formula (1) is reacted with a 3-aminothiophene derivative of formula (2) in the presence of an acid catalyst,

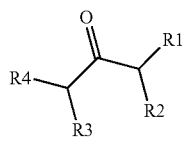

(1)

wherein, in the formula, R1, R2, R3 and R4 each independently represent a hydrogen atom, an alkyl group having 1 to 12 carbon atoms or an alkenyl group having 1 to 12 carbon atoms; at least one of R1, R2, R3 and R4 is an alkyl group having 1 to 12 carbon atoms or an alkenyl group having 1 to 12 carbon atoms; and R1 and R2, R1 and R3, R1 and R4, R2 and R3, R2 and R4, or R3 and R4 may be bonded with each other to form a cycloalkyl group,

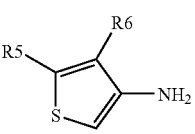

(2)

wherein, in the formula, R5 and R6 each independently represent a hydrogen atom, a halogen atom, a cyano group, a nitro group, an alkyl group having 1 to 12 carbon atoms, an alkenyl group having 1 to 12 carbon atoms, an alkynyl group having 1 to 12 carbon atoms, a phenyl group, a hetero ring, an alkoxy group having 1 to 12 carbon atoms or an alkylthio group having 1 to 12 carbon atoms; and R5 and R6 may be bonded with each other to form a cycloalkyl group,

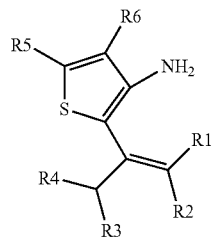

(3a)

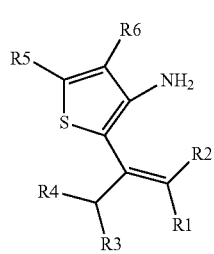

(3b)

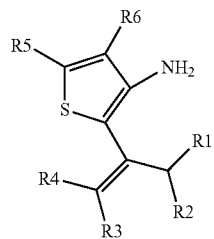

(3c)

(3d)

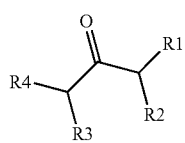

2. The process for producing a 2-alkenyl-3-aminothiophene derivative or a mixture thereof as set forth in claim 1, in which the ketone derivative of formula (1) is reacted with the 3-aminothiophene derivative of formula (2) in the absence of a solvent.

3. The process for producing a 2-alkenyl-3-aminothiophene derivative or a mixture thereof as set forth in claim 1, in which the ketone derivative of formula (1) is reacted with the 3-aminothiophene derivative of formula (2) in a solvent.

4. The process for producing a 2-alkenyl-3-aminothiophene derivative or a mixture thereof as set forth in claim 1, in which, in the formulae (2) and (3a) to (3d), R5 and R6 are each a hydrogen atom.

5. The process for producing a 2-alkenyl-3-aminothiophene derivative or a mixture thereof as set forth in claim 1, in which, in the formulae (1) and (3a) to (3d), R1 represents an isopropyl group, R2, R3 and R4 each represent a hydrogen atom, and R5 and R6 are each a hydrogen atom.

6. A process for producing a 2-alkenyl-3-aminothiophene derivative of formulae (3a) to (3d) or a mixture thereof, in which a salt formed from a 3-aminothiophene derivative of formula (2) and an acid is reacted with a ketone derivative of formula (1), (1)

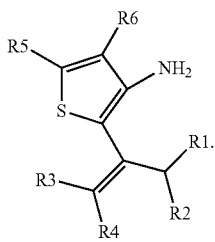

wherein, in the formula, R1, R2, R3 and R4 each independently represent a hydrogen atom, an alkyl group having 1 to 12 carbon atoms or an alkenyl group having 1 to 12 carbon atoms; at least one of R1, R2, R3 and R4 is an alkyl group having 1 to 12 carbon atoms or an alkenyl group having 1 to 12 carbon atoms; and R1 and R2, R1 and R3, R1 and R4, R2 and R3, R2 and R4, or R3 and R4 may be bonded with each other to form a cycloalkyl group, and R5 and R6 each independently represent a hydrogen atom, a halogen atom, a cyano group, a nitro group, an alkyl group having 1 to 12 carbon atoms, an alkenyl group having 1 to 12 carbon atoms, an alkynyl group having 1 to 12 carbon atoms, a phenyl group, a hetero ring, an alkoxy group having 1 to 12 carbon atoms or an alkylthio group having 1 to 12 carbon atoms; and R5 and R6 may be bonded with each other to form a cycloalkyl group, (1)

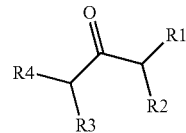

wherein, in the formula, R1, R2, R3 and R4 each independently represent a hydrogen atom, an alkyl group having 1 to 12 carbon atoms or an alkenyl group having 1 to 12 carbon atoms; at least one of R1, R2, R3 and R4 is an alkyl group having 1 to 12 carbon atoms or an alkenyl group having 1 to 12 carbon atoms; and R1 and R2, R1 and R3, R1 and R4, R2 and R3, R2 and R4, or R3 and R4 may be bonded with each other to form a cycloalkyl group, (2)

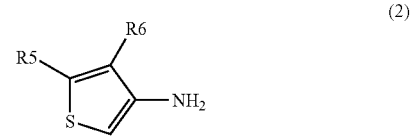

wherein, in the formula, R5 and R6 each independently represent a hydrogen atom, a halogen atom, a cyano group, a nitro group, an alkyl group having 1 to 12 carbon atoms, an alkenyl group having 1 to 12 carbon atoms, an alkynyl group having 1 to 12 carbon atoms, a phenyl group, a hetero ring, an alkoxy group having 1 to 12 carbon atoms or an alkylthio group having 1 to 12 carbon atoms; and R5 and R6 may be bonded with each other to form a cycloalkyl group.

7. The process for producing a 2-alkenyl-3-aminothiophene derivative or a mixture thereof as set forth in claim 6, in which the reaction is carried out in the absence of a solvent.

8. The process for producing a 2-alkenyl-3-aminothiophene derivative or a mixture thereof as set forth in claim 6, in which the reaction is carried out in a solvent.

9. The process for producing a 2-alkenyl-3-aminothiophene derivative or a mixture thereof as set forth in claim 6, in which, in the formulae (2) and (3a) to (3d), R5 and R6 are each a hydrogen atom.

10. The process for producing a 2-alkenyl-3-aminothiophene derivative or a mixture thereof as set forth in claim 7, in which, in the formulae (2) and (3a) to (3d), R5 and R6 are each a hydrogen atom.

11. The process for producing a 2-alkenyl-3-aminothiophene derivative or a mixture thereof as set forth in claim 8, in which, in the formulae (2) and (3a) to (3d), R5 and R6 are each a hydrogen atom.

12. The process for producing a 2-alkenyl-3-aminothiophene derivative or a mixture thereof as set forth in claim 6, in which, in the formulae (1) and (3a) to (3d), R1 represents an isopropyl group, R2, R3 and R4 each represent a hydrogen atom, and R5 and R6 are each a hydrogen atom.

13. The process for producing a 2-alkenyl-3-aminothiophene derivative or a mixture thereof as set forth in claim 7, in which, in the formulae (1) and (3a) to (3d), R1 represents an isopropyl group, R2, R3 and R4 each represent a hydrogen atom, and R5 and R6 are each a hydrogen atom.

14. The process for producing a 2-alkenyl-3-aminothiophene derivative or a mixture thereof as set forth in claim 8, in which, in the formulae (1) and (3a) to (3d), R1 represents an isopropyl group, R2, R3 and R4 each represent a hydrogen atom, and R5 and R6 are each a hydrogen atom.

15. A process for producing a 2-alkenyl-3-aminothiophene derivative of formulae (3'a) to (3'd) or a mixture thereof, in which a ketone derivative of formula (1) is reacted with a 3-aminothiophene derivative of formula (2'), which is obtained from methyl 3-aminothiophene-2-carboxylate as a starting material, in the presence of an acid catalyst,

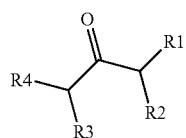

(1)

wherein, in the formula, R1, R2, R3 and R4 each independently represent a hydrogen atom, an alkyl group having 1 to 12 carbon atoms or an alkenyl group having 1 to 12 carbon atoms; at least one of R1, R2, R3 and R4 is an alkyl group having 1 to 12 carbon atoms or an alkenyl group having 1 to 12 carbon atoms; and R1 and R2, R1 and R3, R1 and R4, R2 and R3, R2 and R4, or R3 and R4 may be bonded with each other to form a cycloalkyl group,

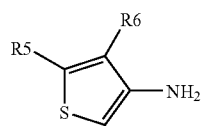

(2')

wherein, in the formula, both of R5 and R6 are hydrogen atoms,

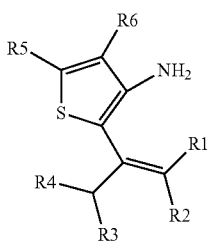

(3'a)

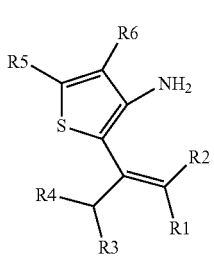

(3'b)

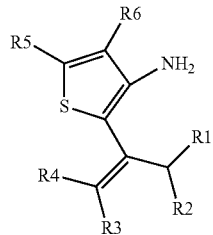

(3'c)

(3'd)

16. The process for producing a 2-alkenyl-3-aminothiophene derivative or a mixture thereof as set forth in claim 15, in which the ketone derivative of formula (1) is reacted with the 3-aminothiophene derivative of formula (2') in the absence of a solvent.

17. The process for producing a 2-alkenyl-3-aminothiophene derivative or a mixture thereof as set forth in claim 15, in which the ketone derivative of formula (1) is reacted with the 3-aminothiophene derivative of formula (2') in a solvent.

18. The process for producing a 2-alkenyl-3-aminothiophene derivative or a mixture thereof as set forth in claim 15, in which, in the formula (1), R1 represents an isopropyl group, and R2, R3 and R4 are each a hydrogen atom, while, in the general formulae (3'a) to (3'd), R1 represents an isopropyl group, and R2, R3, R4, R5 and R6 are each a hydrogen atom.

19. A 2-alkenyl-3-aminothiophene derivative of formulae (3a) to (3d) or a mixture thereof, or a salt formed from said 2-alkenyl-3-aminothiophene derivative and an acid or a mixture thereof,

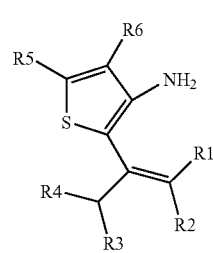

(3a)

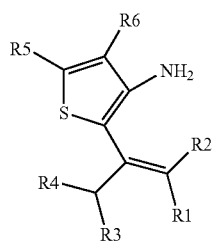
(3b)
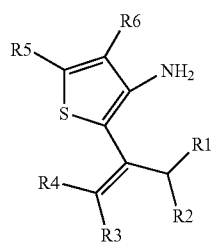
(3c)
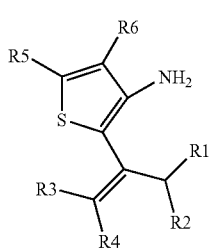
(3d)
wherein, in the formula, R1 represents an isopropyl group, R2, R3 and R4 each represent a hydrogen atom represent a hydrogen atom.
* * * * *